United States Patent [19]

Walker et al.

[11] Patent Number: 5,314,865
[45] Date of Patent: May 24, 1994

[54] CERTAIN ALKYLIDINE AMINOOXYAMIDE COMPOUNDS USEFUL AS HERBICIDES

[75] Inventors: Francis H. Walker, Mill Valley; Don R. Baker, Orinda, both of Calif.

[73] Assignee: ICI Americas Inc., Wilmington, Del.

[21] Appl. No.: 866,912

[22] Filed: Apr. 10, 1992

Related U.S. Application Data

[60] Continuation of Ser. No. 632,890, Dec. 24, 1990, abandoned, which is a division of Ser. No. 287,979, Dec. 21, 1988, Pat. No. 5,002,605.

[51] Int. Cl.$^5$ ................ A01N 43/40; C07D 213/75
[52] U.S. Cl. ......................... 504/244; 546/292
[58] Field of Search ................ 546/292; 504/244

[56] References Cited

U.S. PATENT DOCUMENTS

| 4,423,241 | 12/1983 | Caruso | 560/35 |
| 4,451,286 | 5/1984 | Martin | 71/107 |
| 4,708,734 | 11/1987 | Hayashi et al. | 71/100 |

FOREIGN PATENT DOCUMENTS

| 182407 | 5/1986 | European Pat. Off. | 560/35 |
| 1960910 | 7/1970 | Fed. Rep. of Germany | 564/254 |

OTHER PUBLICATIONS

Chemical Abstracts, vol. 73, Abstract No. 76833b (1970) (Van Dijk et al.).
Chemical Abstracts, vol. 83, Abstract No. 970002 (1975) (Kisfaludy).
Chemical Abstracts, vol. 83, Abstract No. 97043r (1973) (Kisfaludy et al.).
Chemical Abstracts, vol. 90, Abstract No. 22599n (1979) (Shaw).
Chemical Abstracts, vol. 99, Abstract No. 70410b (1983).

*Primary Examiner*—Alan L. Rotman
*Attorney, Agent, or Firm*—Marian T. Thomson; William E. Dickheiser

[57] ABSTRACT

Compounds having the formula

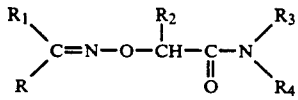

wherein R is $C_1$-$C_6$ lower alkoxy; $C_1$-$C_6$ lower alkylthio; 3- to 6-membered heterocycle or substituted heterocycle; phenyl or substituted phenyl; $R_1$ is hydrogen or $C_1$-$C_3$ lower alkyl; $R_2$ is selected from the group consisting of hydrogen, $C_1$-$C_3$ lower alkyl, $C_3$-$C_6$ cycloalkyl, $C_1$-$C_3$ lower alkylalkoxy or combinations thereof; $R_3$ and $R_4$ are independently selected from the group consisting of hydrogen; $C_1$-$C_6$ lower alkyl; $C_2$-$C_6$ lower alkenyl; $C_2$-$C_6$ lower alkenyl; 3- to 6-membered heterocycle or substituted heterocycle; alkyl heterocycle or substituted alkyl heterocycle; phenyl or substituted phenyl; and where $R_3$ or $R_4$ is a basic heterocycle, herbicidally acceptable organic or inorganic salts thereof are herbicidally active.

15 Claims, No Drawings

CERTAIN ALKYLIDINE AMINOOXYAMIDE COMPOUNDS USEFUL AS HERBICIDES

This is a continuation of application Ser. No. 07/632,890, filed Dec. 24, 1990 abandoned which is a divisional of application Ser. No. 07/287,979 filed Dec. 21, 1988 now U.S. Pat. No. 5,002,605.

BACKGROUND OF THE INVENTION

This invention relates to herbicides and, more particularly, to certain novel substituted alkylidine aminooxyamides.

Certain aminooxy alkanoic acids and esters having the formula $$\begin{array}{c} R_1 \\ \phantom{R_1}\diagdown \\ \phantom{R_1R_1}C=N-O-\underset{\underset{R_2}{|}}{C}H\underset{\underset{}{}}{\overset{\overset{O}{\|}}{C}}X \\ \phantom{R_1}\diagup \\ R_2 \end{array}$$

wherein

X is halogen, OM in which M is an alkali metal, an alkaline earth metal, silver or ammonium cation, OH or $OR_3$ in which $R_3$ is an alkyl or alkoxyalkyl group containing from 1–10 carbon atoms;

R is an alkyl group containing from 2 to 4 carbon atoms;

$R_1$ is a hydrogen atom or an alkyl group containing from 1 to 6 carbon atoms, optionally substituted by one or more halogen atoms; and $R_2$ is an alkyl or alkenyl group containing from 1 to 6 carbon atoms, a phenyl group optionally substituted by one or more substituents selected from a halogen atom, a nitro group, an alkyl, alkylthio or alkoxy group containing from 1 to 4 carbon atoms, each optionally substituted by one or more halogen atoms, or by a methylenedioxy group; or $R_1$ and $R_2$ taken together with the carbon atom to which they are attached form a cyclic hydrocarbyl group containing from 3 to 12 carbon atoms, have been found to be useful as herbicides and plant growth regulators are taught in EPO 182,407, issued to Sanborn et al.

The novel compounds of our invention have been found to be active herbicides possessing herbicidal activity against various species of weeds in the broadest sense, the term "weeds" refers to plants which grow in locations in which they are not desired.

Our invention therefore also relates to a method for controlling undesirable vegetation, comprising applying to a locus where control of such vegetation is desired an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is means to include germinant seeds, emerging seedlings, and established vegetation, including roots and above-ground portions. Such adverse modifying and controlling effects may include all deviations from natural development.

Included with this invention is the composition of matter and method of use.

BRIEF DESCRIPTION OF THE INVENTION

This invention relates to novel herbicidal compounds having the formula $$\begin{array}{c} R_1 \phantom{XXXX} R_2 \phantom{XXXX} R_3 \\ \phantom{R_1}\diagdown \phantom{XX} | \phantom{XXX} \diagup \\ \phantom{R_1R_1}C=N-O-CH-\underset{\underset{}{\overset{\overset{O}{\|}}{}}}{C}-N \\ \phantom{R_1}\diagup \phantom{XXXXXX} \diagdown \\ R \phantom{XXXXX} O \phantom{XXXX} R_4 \end{array}$$

wherein

R is lower alkoxy; lower alkylthio; heterocycle such as, but not limited to, thiazole, thiazole substituted with one or more lower alkyl, halo or lower haloalkyl, thiadiazole, thiadiazole substituted with one or more lower alkyl, halo or lower haloalkyl, thienyl, thienyl substituted with one or more lower alkyl, halo or lower haloalkyl, pyridyl, pyridyl substituted with one or more lower alkyl or halo; phenyl or phenyl substituted with one or more lower alkyl, lower alkoxy, halo, lower haloalkyl, lower haloalkoxy, cyano, nitro, phenoxy, pyridyloxy, lower alkylsulfonyl or combinations thereof;

$R_1$ is hydrogen or lower alkyl;

$R_2$ is selected from the group consisting of hydrogen, lower alkyl, lower cycloalkyl, lower alkylalkoxy or combinations thereof;

$R_3$ and $R_4$ are independently selected from the group consisting of hydrogen; lower alkyl; lower alkenyl; lower alkynyl; pyridyl or pyridyl substituted with one or more halogen or lower alkyl; lower alkylpyridyl or lower alkylpyridyl substituted with one or more halogen or lower alkyl; phenyl or phenyl substituted with one or more lower alkyl, lower alkoxy, halo, lower haloalkyl, lower haloalkoxy, nitro, lower alkylthio, lower alkylsulfonyl or combinations thereof; benzyl, alpha-lower alkyl substituted benzyl, or benzyl substituted with one or more lower alkyl, halo, lower haloalkyl, or combinations thereof; thienyl, thienyl substituted with one or more lower alkyl or halo; piperonyl, furfuryl or methyl naphthyl; or when $R_3$ or $R_4$ are pyridyl, herbicidally acceptable organic or inorganic salts thereof.

DETAILED DESCRIPTION OF THE INVENTION

This invention relates to novel herbicidal compounds having the formula $$\begin{array}{c} R_1 \phantom{XXXX} R_2 \phantom{XXXX} R_3 \\ \phantom{R_1}\diagdown \phantom{XX} | \phantom{XXX} \diagup \\ \phantom{R_1R_1}C=N-O-CH-\underset{\underset{}{\overset{\overset{O}{\|}}{}}}{C}-N \\ \phantom{R_1}\diagup \phantom{XXXXXX} \diagdown \\ R \phantom{XXXXX} O \phantom{XXXX} R_4 \end{array}$$

wherein

R is lower alkoxy; lower alkylthio; heterocycle such as, but not limited to, thiazole, thiazole substituted with one or more lower alkyl, halo or lower haloalkyl, thiadiazole, thiadiazole substituted with one or more lower alkyl, halo or lower haloalkyl, thienyl, thienyl substituted with one or more lower alkyl, halo or lower haloalkyl, pyridyl, pyridyl substituted with one or more lower alkyl or halo, phenyl; or phenyl substituted with one or more lower alkyl, lower alkoxy, halo, lower haloalkyl, lower haloalkoxy, cyano, nitro, phenoxy, pyridyloxy, lower alkylsulfonyl or combinations thereof;

R₁ is hydrogen or lower alkyl;

R₂ is selected from the group consisting of hydrogen, lower alkyl, lower cycloalkyl, lower alkylalkoxy or combinations thereof;

R₃ and R₄ are independently selected from the group consisting of hydrogen; lower alkyl; lower alkenyl; lower alkynyl; pyridyl or pyridyl substituted with one or more halogen or lower alkyl; lower alkylpyridyl or lower alkylpyridyl substituted with one or more halogen or lower alkyl; phenyl or phenyl substituted with one or more lower alkyl, lower alkoxy, halo, lower haloalkyl, lower haloalkoxy, nitro, lower alkylthio, lower alkylsulfonyl or combinations thereof; benzyl, alpha-lower alkyl substituted benzyl, or benzyl substituted with one or more lower alkyl, halo, lower haloalkyl, or combinations thereof; thienyl, thienyl substituted with one or more lower alkyl or halo; piperonyl, furfuryl or methyl naphthyl; or when R₃ or R₄ are pyridyl, herbicidally acceptable organic or inorganic salts thereof.

The compounds of this invention can be prepared via standard methods, including the methods as shown in the following Schemes I-X.

The desired oxime can be reacted at 30°-150° C. in a suitable solvent such as dimethylformamide (DMF) with the desired ester as shown in the following Scheme I:

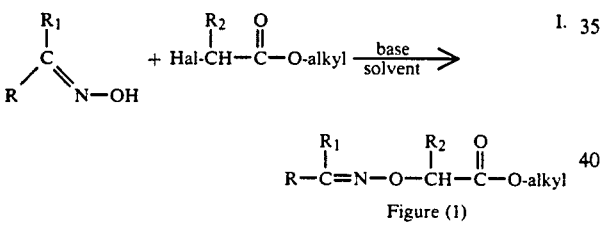

Figure (1)

wherein R and R₂ are as defined above which is then hydrolyzed at 20°-50° C. in the presence of a base such as sodium hydroxide followed by acidification as shown in the following Scheme II:

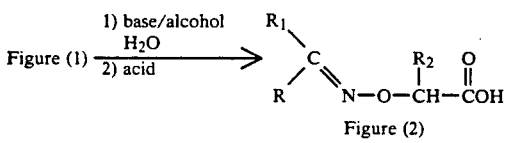

Figure (2)

The resulting acid is then converted to the acid chloride at 40°-80° C. in a solvent such as toluene with phosgene and using DMF as a catalyst to produce the chloride as shown in the following Scheme III:

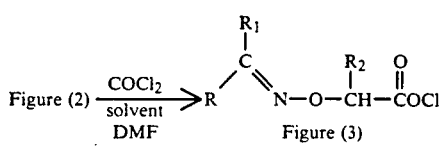

Figure (3)

Said acid chloride can then be reacted with an amine at 20°-40° C. as shown in the following scheme IV:

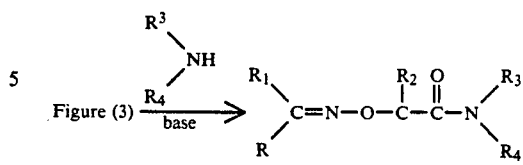

Figure (4)

wherein R₃ and R₄ are as defined above. The acid of the desired oxime can also be reacted with the amine of choice at 20°-30° C. in the presence of carbonyldiimidazole as shown in the following Scheme V:

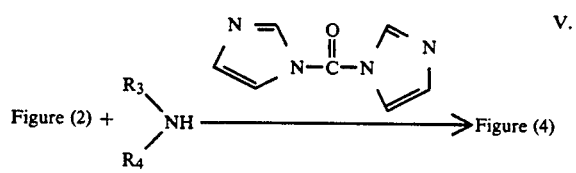

N-Hydroxy phthalimide can be reacted with the desired haloamide at 50°-100° C. in a suitable solvent such as dimethylformamide in the presence of a metal hydride (MH) as shown in the following Scheme VI:

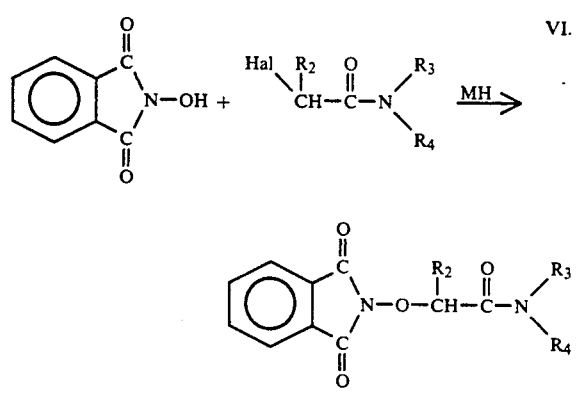

Figure (5)

wherein R₂, R₃, and R₅ are as defined as above, provided that when R₄ is phenyl or pyridyl, R₃ is other than hydrogen, which is then followed by reaction with a hydrazine at 20°-40° C. as shown in the following scheme VII:

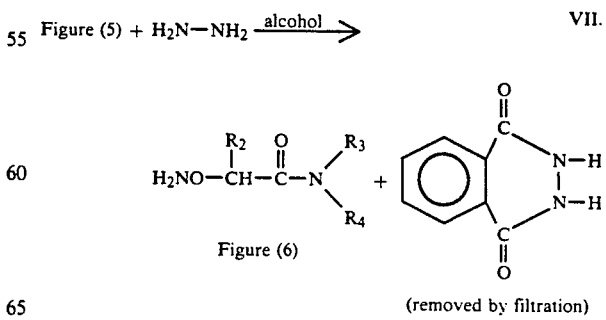

Figure (6)

(removed by filtration)

and then reacted with an aldehyde as shown in the following Scheme VIII:

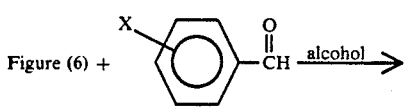

Figure (6) +

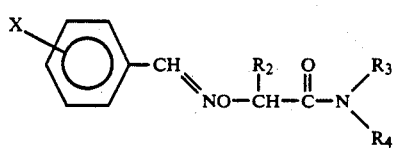

Figure (7)

wherein X is one or more alkyl, alkoxy, halo, haloalkyl, cyano, hydroxy, nitro, phenoxy or combinations thereof, or alternatively, the desired benzaldehyde oxime can be reacted with the desired haloamide at 40°-100° C. in a suitable solvent such as dimethylformamide in the presence of a base such as potassium carbonate as shown in the following Scheme IX:

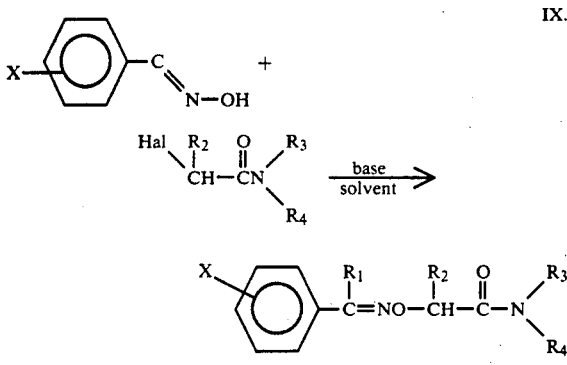

Figure (8)

wherein $R_3$ and $R_4$ are as defined in Scheme VI above. The oxime wherein $R_4$ is a basic heterocycle such as pyridyl can be reacted with an organic or inorganic acid at 0°-40° C. in the presence of a suitable solvent to produce the corresponding salt as shown in scheme X.

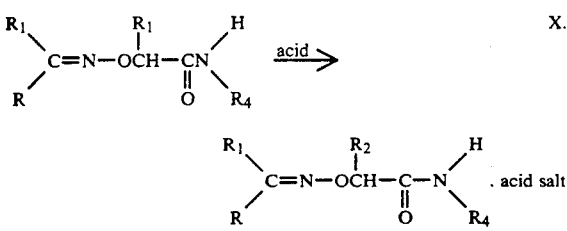

The term "lower alkyl" includes moieties having from about 1 to about 6 carbon atoms such as methyl, ethyl, n-propyl, isopropyl, n-butyl, sec-butyl, isobutyl and tert-butyl, as well as the six pentyls and sixteen hexyls.

The term "lower alkenyl" includes moieties having from about 2 to about 5 carbon atoms such as ethenyl, propenyl, isopropenyl, butenyl, isobutenyl, pentenyl, sec-pentenyl and isopentenyl.

The term "lower alkynyl" includes moieties having from about 2 to about 5 carbon atoms such as ethynyl, propynyl, butynyl, pentynyl and isopentynyl.

The term "lower cycloalkyl" includes unsaturated cyclic moieties having from about 3 to about 6 carbon atoms such as cyclopropyl, cyclobutyl, cyclopentyl and cyclohexyl.

The term "lower alkoxy" includes both straight and branched chain acyclic hydrocarbyl moieties which contain an oxygen in the chain and includes such moieties having from about 1 to about 4 carbon atoms, for example, methoxy, ethoxy, n-propoxy, isopropoxy, n-butoxy, secbutoxy, isobutoxy and tert-butoxy.

The term "halo" includes fluorine, chlorine, bromine or iodine as mono-, di-, tri- and mixed halogen substitutions.

By "heterocycle" is meant a 3- to 6-membered ring compound in which at least one member in the ring is other than carbon such as but not limited to thiazole or thiazole substituted with one or more $C_1$-$C_3$ lower alkyl, halo or $C_1$-$C_3$ lower alkyl, thiadiazole or thiadiazole substituted with one or more $C_1$-$C_3$ lower alkyl, halo or $C_1$-$C_3$ lower haloalkyl; pyridyl or pyridyl substituted with one or more $C_1$-$C_3$ alkyl, halo or $C_1$-$C_3$ lower haloalkyl; thienyl or thienyl substituted with one or more $C_1$-$C_3$ lower alkyl, halo or $C_1$-$C_3$ lower haloalkyl or piperonyl.

Pyridylaminooxyamides of the invention are basic. The pyridyl nitrogen can be at the 2-, 3- or 4-position and the unprotonated nitrogen atom or the pyridyl ring can be protonated by an acid, either organic or inorganic. Representative inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also herbicidal.

The following are examples of the preparation of the compounds of this invention, the structures of which are confirmed by spectroscopy. These examples are offered strictly for purposes of illustration and are intended neither to limit nor to define the invention in any manner.

EXAMPLE I

Preparation of Methyl-2-[1-(3-trifluoromethylphenyl)methylene]-aminooxybutyrate (as shown in Scheme I above)

A solution of 80.0 grams (g) (0.42 mols) of m-trifluoromethylbenzaldoxime in 250 milliliters (ml) of dimethylformamide was added to a solution of 69.1 g (0.50 mol) potassium carbonate in 80 mL of water with rapid stirring. After 15 minutes, 76.6 g (0.42 mol) of methyl-2-bromobutyrate was added to the oxime mixture and this was heated at 80° C. for 2 hours. The mixture was then poured into 1 liter of ice water and extracted sequentially with two 150 mL portions of toluene. The combined toluene extracts were shaken sequentially with three 150 mL portions of brine, dried and evaporated to leave a liquid, 112.3 g, b.p. 122°-125° C./1.25 mm identified as the title compound by infrared (IR), nuclear magnetic resonance (NMR) and mass spectroscopy (MS).

EXAMPLE II

Preparation of 2-[1-(3-Trifluoromethylphenyl)methylene]-aminooxybutyric acid (as shown in Scheme II above)

Ethyl-2-[2-(3-trifluoromethylphenyl)methylene]aminooxybutyrate (141 g, 0.46 mol) was added to a stirred mixture of 38.4 g (0.48 mol) of 50% aqueous sodium hydroxide, 70 mL water and 425 mL ethanol.

The mixture was refluxed for 3 hours, cooled to room temperature, and evaporated under reduced pressure. The residue was taken up in 300 mL water and the resulting mixture was extracted with 150 mL ether. The aqueous layer was removed and acidified with concentrated hydrochloric acid solution. The product separated as an oil and it was removed by extraction with 200 mL ether. The ether extract was shaken with 100 mL brine, dried over MgSO$_4$ and evaporated to leave an oil, 99.2 g, identified by NMR spectroscopy as the acid.

EXAMPLE III

Preparation of N-(2-Pyridylmethyl)-2-[1-(3-trifluoromethylphenyl)methylene]-aminooxybutyramide (as shown in Scheme V above)

A solution of 4.0 g (15 mol) of 2-[1-(3-trifluoromethylphenyl)methylene]aminooxybutyric acid in 100 mL methylene chloride was stirred under nitrogen and 2.4 g (15 mol) of carbonyl diimidazole was added to it. Within 15 minutes CO$_2$ evolution subsided and 1.6 g (15 mol) of 2-(aminomethyl)pyridine were added. The mixture was stirred at room temperature for 3 hours and then allowed to stand overnight. The mixture was next shaken with 100 mL portions of water, saturated sodium bicarbonate and brine followed by drying over magnesium sulfate. Removal of solvent at reduced pressure left an oil, 4.1 g, n$_D^{30}$1.5305, identified as the title compound by NMR, MS and IR.

EXAMPLE IV

Preparation of N-(2-Chlorobenzyl)-2-(N'-phthalimidooxy)-butyramide (as shown in Scheme VI above)

A mixture of 0.3 g (14 mmol) sodium hydride in 80 mL of dry dimethylformamide was stirred under a blanket of nitrogen and 2.3 g (14 mmol) of solid N-hydroxyphthalimide was added to it at 25°-30° C. A deep red color developed. After 0.75 hour 4.0 g (14 mmol) of N-(2-chlorobenzyl)-2-bromobutyramide was added in one portion and the mixture was heated at 100° C. for one hour. During this time the mixture became yellow. The mixture was then poured in 200 mL brine and extracted sequentially with two 100 mL portions of toluene. The combined toluene extracts were shaken sequentially with three 100 mL portions of brine, dried over magnesium sulfate, filtered and evaporated to leave a solid, 4.3 g. The crude product was recrystallized from ethyl alcohol to yield 2.1 g, m.p. 131°–133° C., identified as the title compound by IR, NMR and MS.

EXAMPLE V

Preparation of N-(2-Chlorobenzyl)-1-aminooxybutyramide (as shown in Scheme VII above)

Hydrazine hydrate (1.2 g, 22 mmol) was added to a mixture of 4.0 g (11 mmol) of N-(o-chlorobenzyl)-2-(N'-phthalimidooxy)butyramide in 100 ml ethyl alcohol. There as a slight exotherm and a new solid formed. The mixture was heated at 40° C. for 2 hours and cooled to 5° C. It was filtered and the filtrate was evaporated to leave a solid, 2.4 g, m.p. 65°-70° C. This was identified as the title compound by IR, NMR and MS.

EXAMPLE VI

Preparation of N-(2-Chlorobenzyl)-2-[1-(3-chlorophenyl)methylene]-aminooxybutyramide (as shown in Scheme VIII above)

A mixture of 2.8 g (12 mmol) of N-(2-chlorobenzyl)-2-aminooxybutyramide and 1.6 g (12 mmol) of 3-chlorobenzaldehyde in 75 mL ethanol was heated at reflux for 1 hours. The solvent was then removed at reduced pressure and the residue was taken up in 100 mL methylene chloride, washed with 50 mL brine and dried over magnesium sulfate. Removal of solvent under vacuum left an oil which crystallized, 3.1 g, m.p. 70°-74° C, identified as the title compound by NMR, MS and IR.

EXAMPLE VII

Preparation of N-Benzyl-2-[1-(3-trifluoromethylphenyl)methylene]-aminooxybutyramide (as shown in Scheme IX above)

A mixture of 2.5 g (18 mmol) potassium carbonate, 15 mL water and 50 mL dimethylformamide was stirred and 3.0 g (16 mmol) of m-trifluoromethylbenzaldoxime was added. After 0.5 hour, 4.0 g (16 mmol) of N-benzyl-2-bromobutyramide was added and the mixture was heated at 90° C. for 20 hours. It was then cooled and poured into 250 mL water. The separated organic material was removed by extraction with two 100 mL portions of toluene. The combined toluene extracts were shaken with three 100 mL portions of brine, dried and evaporated under vacuum to leave an oil, 4.5 g. The oil was purified by column chromatography on silica gel Grade 60 using a solution of 65% hexane, 33% ethylacetate, and 2% acetic acid (v/v/v) as eluent. This gave 2.0 g of a solid, m.p. 64°-67° C. identified as the title compound by NMR, MS and IR spectroscopy.

EXAMPLE VIII

Preparation of 2-(Pyridylmethyl)-2-[1-(3-trifluoromethylphenyl)methylene]aminooxybutyramide hydrochloride (as shown in Scheme X above)

4.8 grams (13 mmol) of 2(pyridylmethyl)-2-[1-(3-trifluorophenyl)methylene]aminooxybutyramide were dissolved in 100 mL ethanol and 1.6 g (17 mmol) of concentrated hydrochloric acid were added dropwise. The mixture was evaporated under reduced pressure and 50 mL ethanol was added to the resulting oil and again evaporated to yield 5.4 g of an oil which later crystallized and was identified as the title compound by IR, NMR, and MS.

The following Table I illustrates embodiments of this invention, together with physical data in the form of melting point ranges or refractive indices where such measurements were possible and physical descriptions of the product where neither melting points nor refractice indices could be taken. Structures of the indicated compounds were confirmed by spectroscopy.

TABLE I $$\begin{array}{c} R_1 \\ | \\ R-C=N-O-CH(R_2)-C(=O)-N(R_3)(R_4) \end{array}$$

| Cmpd. No. | R | $R_1$ | $R_2$ | $R_3$ | $R_4$ | Physical Constant $n_D^{30}$ or m.p. °C. |
|---|---|---|---|---|---|---|
| 1 | 3-CF$_3$-C$_6$H$_4$- | —CH$_3$ | —CH$_2$CH$_3$ | H | —CH$_2$-C$_6$H$_5$ | 1.5235 |
| 2 | 3-CF$_3$-C$_6$H$_4$- | —CH$_3$ | —CH$_2$CH$_3$ | H | —CH$_3$ | 83–86 |
| 3 | 3-CF$_3$-C$_6$H$_4$- | —CH$_3$ | —CH$_2$CH$_3$ | H | 2,4-F$_2$-C$_6$H$_3$- | 1.5119 |
| 4 | 3-CF$_3$-C$_6$H$_4$- | —CH$_3$ | —CH$_2$CH$_3$ | H | —CH$_2$-(2-Cl-C$_6$H$_4$) | 1.5305 |
| 5 | 3-CF$_3$-C$_6$H$_4$- | H | —CH$_2$CH$_3$ | H | —CH$_3$ | semisolid |
| 6 | 3-CF$_3$-C$_6$H$_4$- | H | —CH$_2$CH$_3$ | H | —CH$_2$-C$_6$H$_5$ | 64–67 |
| 7 | 3-CF$_3$-C$_6$H$_4$- | H | —CH$_2$CH$_3$ | H | —CH$_2$-(2-Cl-C$_6$H$_4$) | 50–57 |
| 8 | 3,4-Cl$_2$-C$_6$H$_3$- | —CH$_3$ | —CH$_3$ | H | —CH$_2$-C$_6$H$_5$ | 72–75 |
| 9 | 3,4-Cl$_2$-C$_6$H$_3$- | —CH$_3$ | —CH$_2$CH$_3$ | H | —CH$_2$-C$_6$H$_5$ | 62–70 |
| 10 | 3,4-Cl$_2$-C$_6$H$_3$- | —CH$_3$ | —CH$_2$CH$_3$ | H | —CH$_2$-(2-Cl-C$_6$H$_4$) | oily solid |

TABLE I-continued $$\underset{R}{\overset{R_1}{C}}=N-O-\underset{\underset{O}{\overset{R_2}{C}}}{CH}-\underset{\underset{O}{\overset{}{C}}}{\overset{R_3}{N}}\overset{R_3}{\underset{R_4}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 11 | 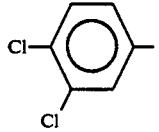 (3,4-diCl-phenyl) | —CH$_3$ | —CH$_2$CH$_3$ | H | 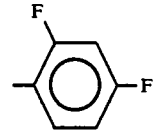 (2,4-diF-phenyl) | 1.5612 |
| 12 | 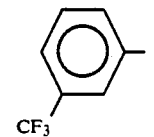 (3-CF$_3$-phenyl) | —CH$_3$ | —CH$_3$ | H | —CH$_2$ | 1.5264 |
| 13 | 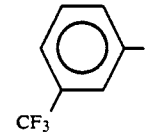 (3-CF$_3$-phenyl) | —CH$_3$ | —CH(CH$_3$)$_2$ | H | —CH$_2$ | 1.5200 |
| 14 | CH$_3$CH$_2$O— | CH$_3$ | —CH$_2$CH$_3$ | H | CH$_2$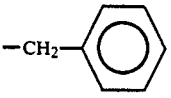 | 1.5085 |
| 15 | 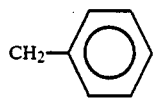 (3-Cl-phenyl) | —CH$_3$ | —CH$_2$CH$_3$ | H | —CH$_2$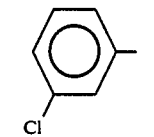 | 1.5640 |
| 16 | 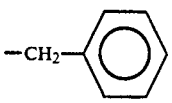 (3-CF$_3$-phenyl) | —CH$_3$ | —CH$_2$CH$_3$ | H | —CH$_2$CH=CH$_2$ | 52–55 |
| 17 | 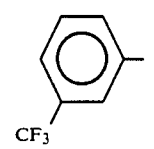 (3-CF$_3$-phenyl) | —CH$_3$ | —CH$_2$CH$_3$ | H | —CH$_2$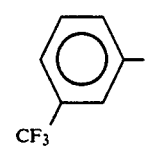 | 1.5236 |
| 18 | 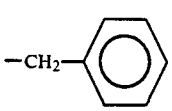 (3-CF$_3$-phenyl) | —C$_2$H$_5$ | —CH$_2$CH$_3$ | H | —CH$_2$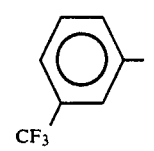 | 1.5215 |
| 19 | 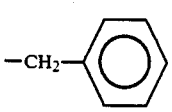 (3-CF$_3$-phenyl) | —CH$_3$ | —CH$_2$CH$_3$ | H | —CH(CH$_3$)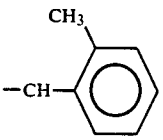 | 1.5205 |

TABLE I-continued

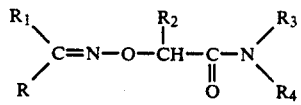

| Cmpd. No. | R | $R_1$ | $R_2$ | $R_3$ | $R_4$ | Physical Constant $n_D^{30}$ or m.p. °C. |
|---|---|---|---|---|---|---|
| 20 | 3-CF$_3$-C$_6$H$_4$- | —CH$_3$ | —CH$_2$CH$_3$ | H | CH$_2$C≡CH | 53–56 |
| 21 | 3-CF$_3$-C$_6$H$_4$- | —CH$_3$ | —CH$_2$CH$_3$ | —CH$_2$CH=CH$_2$ | —CH$_2$CH=CH$_2$ | 1.4958 |
| 22 | 3,4-Cl$_2$-C$_6$H$_3$- | H | —CH$_2$CH$_3$ | H | —CH$_2$-C$_6$H$_5$ | 1.5745 |
| 23 | 3-CF$_3$-C$_6$H$_4$- | H | —CH$_3$ | H | —CH$_2$-C$_6$H$_5$ | 64–66 |
| 24 | 3-CF$_3$-C$_6$H$_4$- | H | —CH(CH$_3$)$_2$ | H | —CH$_2$-C$_6$H$_5$ | opaque oil |
| 25 | 3-CF$_3$-C$_6$H$_4$- | H | —CH$_2$CH$_3$ | H | —CH$_2$C≡CH | glass |
| 26 | 3-CF$_3$-C$_6$H$_4$- | H | —CH$_2$CH$_3$ | H | 2,4-F$_2$-C$_6$H$_3$- | 43–48 |
| 27 | 3-CN-C$_6$H$_4$- | H | —CH$_2$CH$_3$ | H | —CH$_2$-(2-Cl-C$_6$H$_4$) | 105–110 |
| 28 | CH$_3$CH$_2$O— | CH$_3$ | —CH$_2$CH$_3$ | H | —CH$_2$-C$_6$H$_5$ | 1.5195 |

TABLE I-continued $$\underset{R}{\overset{R_1}{C}}=N-O-\underset{}{\overset{R_2}{CH}}-\underset{\overset{\|}{O}}{C}-N\overset{R_3}{\underset{R_4}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 29 | 3-(N≡C)-C₆H₄ | H | —CH₂CH₃ | H | —CH₂-C₆H₅ | 137–140 |
| 30 | 2-Cl-3-CF₃-C₆H₃ | H | —CH₂CH₃ | H | —CH₂-(2-Cl-C₆H₄) | 1.5425 |
| 31 | 2-Cl-3-CF₃-C₆H₃ | H | —CH₂CH₃ | H | —CH₂-C₆H₅ | 1.5370 |
| 32 | 3-CF₃-C₆H₄ | H | —CH₂CH₂CH₃ | H | —CH₂-C₆H₅ | oily solid |
| 33 | 3-CF₃-C₆H₄ | H | —CH₂CH₂CH₃ | H | —CH₂-(2-Cl-C₆H₄) | waxy solid |
| 34 | 3-Cl-C₆H₄ | H | —CH₂CH₃ | H | —CH₂-C₆H₅ | 70–76 |
| 35 | 3-Cl-C₆H₄ | H | —CH₂CH₃ | H | —CH₂-(2-Cl-C₆H₄) | 70–74 |
| 36 | 3-CF₃-C₆H₄ | H | —CH₂CH₃ | H | —CH₂-(2-F-C₆H₄) | 1.5161 |
| 37 | 2,4-F₂-C₆H₃ | H | —CH₂CH₃ | H | —CH₂-C₆H₅ | 65–70 |

TABLE I-continued $$\underset{R}{\overset{R_1}{C}}=N-O-\underset{\overset{\|}{O}}{\overset{R_2}{C}H}-\underset{\overset{\|}{O}}{C}-N\overset{R_3}{\underset{R_4}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 38 | 3-CF₃-C₆H₄ | H | —CH₂CH₃ | H | —CH₂-C₆H₄-4-Cl | 1.5333 |
| 39 | 3-CF₃-C₆H₄ | H | —CH₂CH₃ | H | —CH₂-C₆H₄-4-F | 1.5182 |
| 40 | 3-CF₃-C₆H₄ | H | —CH₂OCH₃ | H | —CH₂-C₆H₅ | 1.5093 |
| 41 | 3-CN-C₆H₄ | H | —CH₂OCH₃ | H | —CH₂-C₆H₅ | oily solid |
| 42 | 3-CF₃-C₆H₄ | H | —CH₂CH₃ | H | —CH₂-C₆H₄-2-Cl | 1.5338 |
| 43 | 3-CF₃-C₆H₄ | H | —CH₂CH₃ | H | —CH₂-C₆H₃-2,4-Cl₂ | opaque oil |
| 44 | 3-CF₃-C₆H₄ | H | —CH₂CH₃ | H | —CH₂-C₆H₄-2-OCH₃ | 1.5310 |
| 45 | 3-CF₃-C₆H₄ | H | —CH₂CH₃ | H | —CH₂-C₆H₃-3,4-Cl₂ | 1.5410 |
| 46 | 3-CF₃-C₆H₄ | H | —CH₂CH₃ | H | —CH₂-C₆H₄-2-CH₃ | 65-72 |

TABLE I-continued $$R_1\underset{R}{\overset{}{C}}=N-O-\overset{R_2}{\underset{}{C}H}-\underset{\underset{O}{\|}}{C}-N\underset{R_4}{\overset{R_3}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 47 | $CH_3CH_2O-$ | $-CH_3$ | $-CH_2OCH_3$ | H | $-CH_2$-phenyl | 1.5250 |
| 48 | 3-$CF_3$-phenyl | H | $-CH_2CH_3$ | H | $-CH_2$-(benzo[1,3]dioxole) | 1.5385 |
| 49 | 3-$CF_3$-phenyl | H | $-CH_2CH_3$ | H | $-CH_2$-(2-thienyl) | 1.5356 |
| 50 | $CH_3CH_2S-$ | $-CH_3$ | $-CH_2CH_3$ | H | $-CH_2$-phenyl | 1.5390 |
| 51 | 3-$CF_3$-phenyl | H | $-CH_2CH_3$ | H | $-CH_2$-(3-pyridyl) | 1.5270 |
| 52 | $CH_3CH_2S-$ | $-CH_3$ | $-CH_2CH_3$ | H | $-CH_2$-(2-pyridyl) | viscous oil |
| 53 | $CH_3CH_2S-$ | $-CH_3$ | $-CH_2CH_3$ | H | $-CH_2$-(1-naphthyl) | 1.5630 |
| 54 | 3-$CF_3$-phenyl | H | $-CH_2CH_3$ | H | 4-F-phenyl | 82–90 |
| 55 | 3-$CF_3$-phenyl | H | $-CH_2CH_3$ | H | $-CH_2$-(2-pyridyl) | 1.5305 |

TABLE I-continued $$R\overset{R_1}{\underset{}{C}}=N-O-\overset{R_2}{\underset{}{CH}}-\overset{}{\underset{O}{C}}-N\overset{R_3}{\underset{R_4}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 56 | 3-CF₃-C₆H₄- | H | —CH₂CH₃ | H | 4-Cl-C₆H₄- | 1.5348 |
| 57 | 3-CF₃-C₆H₄- | H | —CH₂CH₃ | H | —CH₂-(pyridyl) | semisolid |
| 58 | CH₃CH₂O— | CH₃ | —CH₂CH₃ | H | —CH₂-(2-F-C₆H₄) | 53–60 |
| 59 | 3-CF₃-C₆H₄- | H | —CH₂CH₃ | H | —CH₂-(3-F-C₆H₄) | 1.5191 |
| 60 | 2,4-F₂-C₆H₃- | H | —CH₂CH₃ | H | —CH₂-(2-Cl-C₆H₄) | 93–100 |
| 61 | 2,4-F₂-C₆H₃- | H | —CH₂CH₃ | H | —CH₂-(2-F-C₆H₄) | 63–67 |
| 62 | 2-Cl-3-CF₃-C₆H₃- | H | —CH₂CH₃ | —CH₃ | —CH₂-C₆H₅ | 1.5398 |
| 63 | 3-CF₃-C₆H₄- | H | —CH₂CH₃ | H | —CH₂-(2,4-F₂-C₆H₃) | 1.5162 |
| 64 | 2-Cl-C₆H₄- | H | —CH₂CH₃ | H | —CH₂-C₆H₅ | 95–97 |

TABLE I-continued $$R_1\text{-}C(R)=N\text{-}O\text{-}CH(R_2)\text{-}C(=O)\text{-}N(R_3)(R_4)$$

| Cmpd. No. | R | $R_1$ | $R_2$ | $R_3$ | $R_4$ | Physical Constant $n_D^{30}$ or m.p. °C. |
|---|---|---|---|---|---|---|
| 65 | 3-CF$_3$-phenyl | H | —CH$_2$CH$_3$ | H | —CH$_2$-(2,5-difluorophenyl) | 1.5115 |
| 66 | 2-F-phenyl | H | —CH$_2$CH$_3$ | H | —CH$_2$-phenyl | 67–73 |
| 67 | 3-F-phenyl | H | —CH$_2$CH$_3$ | H | —CH$_2$-phenyl | 70–75 |
| 68 | 3-CF$_3$-phenyl | H | —CH$_2$CH$_3$ | H | 2-F-phenyl | 1.5195 |
| 69 | 3-CF$_3$-phenyl | H | —CH$_2$CH$_3$ | H | —CH$_2$-(3-F-phenyl) | 1.5185 |
| 70 | 2,4-difluorophenyl | H | —CH$_2$CH$_3$ | H | 2,4-difluorophenyl | oily solid |
| 71 | 2,4-difluorophenyl | H | —CH$_2$CH$_3$ | H | —CH$_2$-(2-CH$_3$-phenyl) | 88–93 |
| 72 | 2,4-difluorophenyl | H | —CH$_2$CH$_3$ | H | 4-F-phenyl | 82–85 |
| 73 | 2,4-difluorophenyl | H | —CH$_2$CH$_3$ | H | 2-F-phenyl | oily solid |

TABLE I-continued $$R_1\diagdown C=N-O-\underset{R_2}{\underset{|}{CH}}-\underset{O}{\underset{\|}{C}}-N\diagup\underset{R_4}{\overset{R_3}{\diagdown}}$$
$$R\diagup$$

| Cmpd. No. | R | $R_1$ | $R_2$ | $R_3$ | $R_4$ | Physical Constant $n_D^{30}$ or m.p. °C. |
|---|---|---|---|---|---|---|
| 74 | 3-pyridyl | H | —CH$_2$CH$_3$ | H | —CH$_2$-phenyl | 1.5660 |
| 75 | 3-pyridyl | H | —CH$_2$CH$_3$ | H | —CH$_2$-(2-Cl-phenyl) | 60–65 |
| 76 | 3-CF$_3$-phenyl | H | —CH$_2$CH$_3$ | H | 2-Br-phenyl | dark oil |
| 77 | 3-CF$_3$-phenyl | H | —CH$_2$CH$_3$ | H | —CH$_2$-(2-Br-phenyl) | oily solid |
| 78 | 3-CF$_3$-phenyl | H | —CH$_2$CH$_3$ | H | phenyl | 67–72 |
| 79 | 3-CF$_3$-phenyl | H | —CH$_2$CH$_3$ | H | 2-Cl-phenyl | oily solid |
| 80 | 3-CF$_3$-phenyl | H | —CH$_2$CH$_3$ | H | 4-Cl-phenyl | viscous oil |
| 81 | 3-Cl-phenyl | H | —CH$_2$CH$_3$ | H | 2,3-diF-phenyl | 73–85 |
| 82 | 3-Cl-phenyl | H | —CH$_2$CH$_3$ | H | —CH$_2$-(2-F-phenyl) | 52–57 |
| 83 | 3-Cl-phenyl | H | —CH$_2$CH$_3$ | H | —CH$_2$-(2-CH$_3$-phenyl) | 95–98 |

TABLE I-continued $$\underset{R}{\overset{R_1}{\underset{}{C}}}=N-O-\underset{R_2}{\overset{R_2}{\underset{}{C}H}}-\underset{\overset{\|}{O}}{C}-N\underset{R_4}{\overset{R_3}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 84 | 3-Cl-phenyl | H | —CH$_2$CH$_3$ | H | 3-Cl-phenyl | oily solid |
| 85 | 3-CF$_3$-phenyl | H | —CH$_2$CH$_3$ | H | 3-Cl-phenyl | oily solid |
| 86 | 4-phenoxyphenyl | H | —CH$_2$CH$_3$ | H | —CH$_2$-phenyl | 1.5842 |
| 87 | 4-phenoxyphenyl | H | —CH$_2$CH$_3$ | H | —CH$_2$-(2-Cl-phenyl) | 78–81 |
| 88 | 3-CF$_3$-phenyl | H | —CH$_2$CH$_3$ | H | —CH$_2$-(2-CF$_3$-phenyl) | 1.5010 |
| 89 | 3-Cl-phenyl | H | —CH$_2$CH$_3$ | H | —CH$_2$-(2-CF$_3$-phenyl) | oily solid |
| 90 | 3-CF$_3$-phenyl | H | —CH$_2$CH$_3$ | H | —CH$_2$-(2,6-diF-phenyl) | 53–56 |
| 91 | 3-Cl-phenyl | H | —CH$_2$CH$_3$ | H | —CH$_2$-(2,6-diF-phenyl) | 115–120 |

TABLE I-continued $$R_1\phantom{xx}R_2\phantom{xx}R_3$$
$$R-C=N-O-CH-C-N-R_4$$
$$\phantom{xxxxxxxxxxxx}\|$$
$$\phantom{xxxxxxxxxxxx}O$$

| Cmpd. No. | R | $R_1$ | $R_2$ | $R_3$ | $R_4$ | Physical Constant $n_D^{30}$ or m.p. °C. |
|---|---|---|---|---|---|---|
| 92 | 3-CF$_3$-C$_6$H$_4$- | H | -CH$_2$CH$_3$ | H | 3-Cl-4-F-C$_6$H$_3$- | dark oil |
| 93 | 3-CF$_3$-C$_6$H$_4$- | H | -CH$_2$CH$_3$ | H | -CH$_2$CH$_2$- | 1.5249 |
| 94 | 3-OCH$_3$-C$_6$H$_4$- | H | -CH$_2$CH$_3$ | H | C$_6$H$_5$- | 1.5625 |
| 95 | 3-CH$_3$-C$_6$H$_4$- | H | -CH$_2$CH$_3$ | H | C$_6$H$_5$- | 1.5621 |
| 96 | 3-NO$_2$-C$_6$H$_4$- | H | -CH$_2$CH$_3$ | H | C$_6$H$_5$- | 98-103 |
| 97 | 3-Br-C$_6$H$_4$- | H | -CH$_2$CH$_3$ | H | -CH$_2$-C$_6$H$_5$ | 75-80 |
| 98 | 3,5-Cl$_2$-C$_6$H$_3$- | H | -CH$_2$CH$_3$ | H | -CH$_2$-C$_6$H$_5$ | 100-105 |
| 99 | 3,5-(CF$_3$)$_2$-C$_6$H$_3$- | H | -CH$_2$CH$_3$ | H | -CH$_2$-(2-Cl-C$_6$H$_4$) | 82-88 |
| 100 | CH$_3$CH$_2$O- | CH$_3$- | -CH$_2$CH$_3$ | H | -CH$_2$-(2-CH$_3$-C$_6$H$_4$) | 68-72 |

TABLE I-continued $$R_1\text{-}C(R)=N\text{-}O\text{-}CH(R_2)\text{-}C(=O)\text{-}N(R_3)(R_4)$$

| Cmpd. No. | R | $R_1$ | $R_2$ | $R_3$ | $R_4$ | Physical Constant $n_D^{30}$ or m.p. °C. |
|---|---|---|---|---|---|---|
| 101 | $CH_3CH_2O-$ | $CH_3-$ | $-CH_2CH_3$ | H | 2,4-difluorophenyl | 43–46 |
| 102 | $CH_3CH_2O-$ | $CH_3-$ | $-CH_2CH_3$ | H | $-CH_2-$(2,6-difluorophenyl) | 1.4895 |
| 103 | $CH_3CH_2O-$ | $CH_3-$ | $-CH_2CH_3$ | H | $-CH_2-$(2-pyridyl) | 1.5063 |
| 104 | 3-$CF_3$-phenyl | H | $-CH_2CH_3$ | H | $-CH_2-$(2,6-dichlorophenyl) | 60–63 |
| 105 | 3-$CF_3$-phenyl | H | $-CH_2CH_3$ | H | 3-chloro-2,4-difluorophenyl | waxy solid |
| 106 | 3-$CF_3$-phenyl | H | $-CH_3CH_3$ | H | 4-fluoro-3-trifluoromethylphenyl | 85–88 |
| 107 | 3-$CF_3$-phenyl | H | $-CH_2CH_3$ | H | 2,4-dimethylphenyl | 65–70 |
| 108 | 3-$CF_3$-phenyl | H | $-CH_2CH_3$ | H | $-CH_2-$(2,4-difluorophenyl) | 68–72 |
| 109 | 3-$CF_3$-phenyl | H | $-CH_2CH_3$ | H | $-CH_2-$(3,4-difluorophenyl) | 56–59 |

TABLE I-continued $$\underset{R}{\overset{R_1}{\subset}} = N - O - \underset{R_2}{\overset{R_2}{CH}} - \underset{O}{\overset{\parallel}{C}} - N \underset{R_4}{\overset{R_3}{\diagdown}}$$

| Cmpd. No. | R | $R_1$ | $R_2$ | $R_3$ | $R_4$ | Physical Constant $n_D^{30}$ or m.p. °C. |
|---|---|---|---|---|---|---|
| 110 | 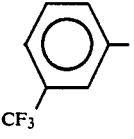 CF$_3$ | H | —CH$_2$CH$_3$ | H | 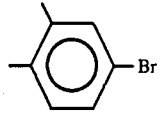 F, Br | 1.5432 |
| 111 | 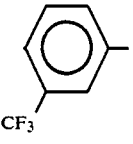 CF$_3$ | H | —CH$_2$CH$_3$ | H | 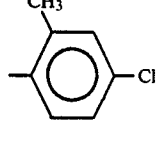 CH$_3$, Cl | 85–87 |
| 112 | 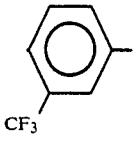 CF$_3$ | H | —CH$_2$CH$_3$ | H | 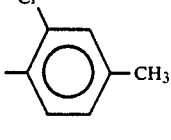 Cl, CH$_3$ | 1.5360 |
| 113 | 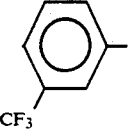 CF$_3$ | H | —CH$_2$CH$_3$ | H | 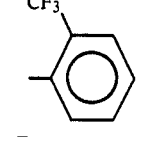 CF$_3$ | 1.5008 |
| 114 | 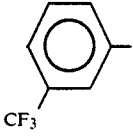 CF$_3$ | H | —CH$_2$CH$_3$ | H | 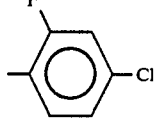 F, Cl | 1.5295 |
| 115 | 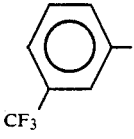 CF$_3$ | H | —CH$_2$CH$_3$ | H | 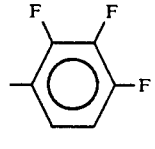 F, F, F | 1.5055 |
| 116 | 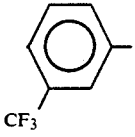 CF$_3$ | H | —CH$_2$CH$_3$ | H | 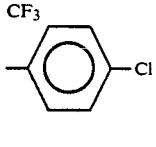 CF$_3$, Cl | 1.5805 |
| 117 | 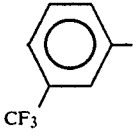 CF$_3$ | H | H | —CH$_2$CH$_3$ | 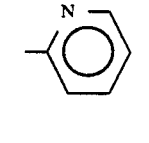 N | 1.5282 |
| 118 | 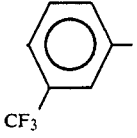 CF$_3$ | H | H | —CH$_2$CH$_3$ | 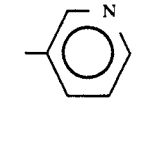 N | 1.5355 |

TABLE I-continued $$\begin{array}{c} R_1 \quad R_2 \quad R_3 \\ \underset{R}{C}=N-O-CH-\underset{\underset{O}{\|}}{C}-N \\ \quad\quad\quad\quad\quad\quad\quad R_4 \end{array}$$

| Cmpd. No. | R | $R_1$ | $R_2$ | $R_3$ | $R_4$ | Physical Constant $n_D^{30}$ or m.p. °C. |
|---|---|---|---|---|---|---|
| 119 | 3-CF₃-C₆H₄- | H | H | —CH₂CH₃ | pyridyl | oily solid |
| 120 | 3-CF₃-C₆H₄- | H | H | —CH₂CH₃ | 2,4,5-trichlorophenyl | 59–62 |
| 121 | 3-CF₃-C₆H₄- | H | H | —CH₂CH₃ | 2-Br-4-F-phenyl | 1.5338 |
| 122 | 3-CF₃-C₆H₄- | H | H | —CH₂CH₃ | 4-CF₃-phenyl | 1.5066 |
| 123 | 3-CF₃-C₆H₄- | H | H | —CH₂CH₃ | —CH₂-(2,5-diCH₃-phenyl) | 55–60 |
| 124 | 3-CF₃-C₆H₄- | H | H | —CH₂CH₃ | —CH₂-(6-CH₃-pyridin-2-yl) | 1.5204 |
| 125 | 3-NO₂-C₆H₄- | H | H | —CH₂CH₃ | 2,4-diCl-phenyl | 76–78 |
| 126 | 3-NO₂-C₆H₄- | H | H | —CH₂CH₃ | 2,4-diF-phenyl | 75–80 |

TABLE I-continued $$\underset{R}{\overset{R_1}{\underset{}{C}}}=N-O-\underset{}{\overset{R_2}{\underset{}{CH}}}-\underset{\overset{\|}{O}}{C}-N\underset{R_4}{\overset{R_3}{\diagup}}$$

| Cmpd. No. | R | $R_1$ | $R_2$ | $R_3$ | $R_4$ | Physical Constant $n_D^{30}$ or m.p. °C. |
|---|---|---|---|---|---|---|
| 127 | 3-nitrophenyl | H | H | —CH$_2$CH$_3$ | —CH$_2$-(2-pyridyl) | 80–83 |
| 128 | 3-nitrophenyl | H | H | —CH$_2$CH$_3$ | —CH$_2$-(2-methylphenyl) | 97–100 |
| 129 | 3-nitrophenyl | H | H | —CH$_2$CH$_3$ | —CH$_2$-(2-chlorophenyl) | 93–97 |
| 130 | 3-nitrophenyl | H | H | —CH$_2$CH$_3$ | —CH$_2$-(2-fluorophenyl) | 92–95 |
| 131 | 3-CF$_3$-phenyl | H | H | —CH$_2$CH$_3$ | 2-nitro-4-chlorophenyl | 58–62 |
| 132 | 3-CF$_3$-phenyl | H | H | —CH$_2$CH$_3$ | 2-chloro-4-fluorophenyl | 1.5275 |
| 133 | 3,5-bis(CF$_3$)-phenyl | H | H | H | 2-chloro-4-nitrophenyl | 43–48 |
| 134 | 3,5-bis(CF$_3$)-phenyl | H | H | H | 2-nitro-4-fluorophenyl | 1.5406 |

TABLE I-continued $$R_1\text{-}C(R)=N\text{-}O\text{-}CH(R_2)\text{-}C(=O)\text{-}N(R_3)(R_4)$$

| Cmpd. No. | R | R$_1$ | R$_2$ | R$_3$ | R$_4$ | Physical Constant n$_D^{30}$ or m.p. °C. |
|---|---|---|---|---|---|---|
| 135 | 3-CF$_3$-C$_6$H$_4$- | H | H | H | -CH$_2$-(2,4-di-CH$_3$-C$_6$H$_3$) | 94–97 |
| 136 | 3-NO$_2$-C$_6$H$_4$- | H | H | H | -CH$_2$-(2-CF$_3$-C$_6$H$_4$) | 90–92 |
| 137 | 3-F-C$_6$H$_4$- | H | H | H | -CH$_2$-(2-F-C$_6$H$_4$) | 63–69 |
| 138 | 3-F-C$_6$H$_4$- | H | H | H | -CH$_2$-(2-pyridyl) | oily solid |
| 139 | 3-F-C$_6$H$_4$- | H | H | H | -(3,4-di-F-C$_6$H$_3$) | 60–63 |
| 140 | 3-F-C$_6$H$_4$- | H | H | H | -CH$_2$-(2-Cl-C$_6$H$_4$) | 62–64 |
| 141 | 3-F-C$_6$H$_4$- | H | H | H | -(2,4-di-Cl-C$_6$H$_3$) | 1.5764 |
| 142 | 3-F-C$_6$H$_4$- | H | H | H | -CH$_2$-(2-CF$_3$-C$_6$H$_4$) | 70–71 |
| 143 | 3-F-C$_6$H$_4$- | H | H | H | -CH$_2$-(2-CH$_3$-C$_6$H$_4$) | 88–91 |

TABLE I-continued $$R_1\text{-}C(R)=N\text{-}O\text{-}CH(R_2)\text{-}C(=O)\text{-}N(R_3)(R_4)$$

| Cmpd. No. | R | $R_1$ | $R_2$ | $R_3$ | $R_4$ | Physical Constant $n_D^{30}$ or m.p. °C. |
|---|---|---|---|---|---|---|
| 144 | 3-F-phenyl | H | H | H | 4-F-phenyl | 65–68 |
| 145 | 3-NO$_2$-phenyl | H | H | H | 4-F-phenyl | 65–70 |
| 146 | 3-CF$_3$-phenyl | H | H | H | 2-Br-4-Cl-phenyl | 1.5551 |
| 147 | 3-CF$_3$-phenyl | H | H | H | 2-F-4-Br-phenyl | dark oil |
| 148 | 3-CF$_3$-phenyl | H | H | H | 2-Cl-4-Br-phenyl | 1.5582 |
| 149 | 3-NO$_2$-phenyl | H | —CH$_2$CH$_3$ | H | —CH$_2$-(6-CH$_3$-pyridin-2-yl) | 1.5676 |
| 150 | 3-Br-phenyl | H | —CH$_2$CH$_3$ | H | 2,4-di-F-phenyl | 87–92 |
| 151 | 3-Br-phenyl | H | —CH$_2$CH$_3$ | H | pyridin-2-yl | 1.5835 |
| 152 | 3-Br-phenyl | H | —CH$_2$CH$_3$ | H | —CH$_2$-(2-Cl-phenyl) | 90–95 |

TABLE I-continued $$\underset{R}{\overset{R_1}{C}}=N-O-\underset{R_2}{\overset{R_2}{C}H}-\underset{\overset{\parallel}{O}}{C}-N\underset{R_4}{\overset{R_3}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 153 | 3-Br-C6H4 | H | —CH2CH3 | H | —CH2-(2-CH3-C6H4) | 58–65 |
| 154 | 3-Br-C6H4 | H | —CH2CH3 | H | —CH2-(2-F-C6H4) | 55–60 |
| 155 | 3-Br-C6H4 | H | —CH2CH3 | H | 2,4-Cl2-C6H3 | 1.6026 |
| 156 | 3-Br-C6H4 | H | —CH2CH3 | H | —CH2-(2-CF3-C6H4) | 87–92 |
| 157 | 3-CF3-C6H4 | H | —CH2CH3 | H | 2-SCH3-C6H4 | 1.5486 |
| 158 | 3-CF3-C6H4 | H | —CH2CH3 | H | 4-SCH3-C6H4 | 95–98 |
| 159 | 3-CH3-C6H4 | H | —CH2CH3 | H | 2-pyridyl | 1.5611 |
| 160 | 3-CH3-C6H4 | H | —CH2CH3 | H | —CH2-(2-F-C6H4) | 58–62 |
| 161 | 3-CH3-C6H4 | H | —CH2CH3 | H | —CH2-(2-Cl-C6H4) | 75–78 |

TABLE I-continued $$R_1\!-\!\underset{R}{\overset{}{C}}\!=\!N\!-\!O\!-\!\underset{}{\overset{R_2}{C}}H\!-\!\underset{\underset{O}{\|}}{C}\!-\!N\!\underset{R_4}{\overset{R_3}{<}}$$

| Cmpd. No. | R | $R_1$ | $R_2$ | $R_3$ | $R_4$ | Physical Constant $n_D^{30}$ or m.p. °C. |
|---|---|---|---|---|---|---|
| 162 | 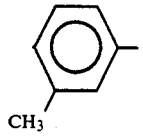 3-CH₃-C₆H₄ | H | —CH₂CH₃ | H | 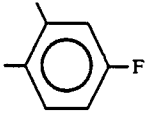 2,4-difluorophenyl | 63–65 |
| 163 | 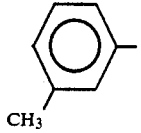 3-CH₃-C₆H₄ | H | —CH₂CH₃ | H | 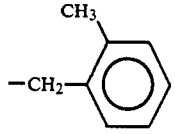 —CH₂-(2-CH₃-C₆H₄) | 82–84 |
| 164 | 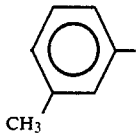 3-CH₃-C₆H₄ | H | —CH₂CH₃ | H | 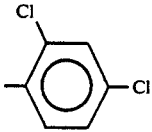 2,4-dichlorophenyl | 47–49 |
| 165 | 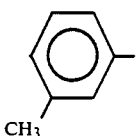 3-CH₃-C₆H₄ | H | —CH₂CH₃ | H | 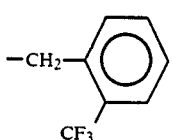 —CH₂-(2-CF₃-C₆H₄) | 52–55 |
| 166 | 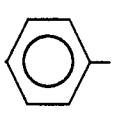 C₆H₅ | H | —CH₂CH₃ | H | 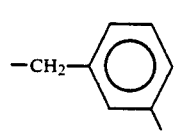 —CH₂-(3-CF₃-C₆H₄) | 65–68 |
| 167 | 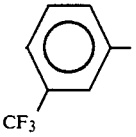 3-CF₃-C₆H₄ | H | —CH₂CH₃ | H | 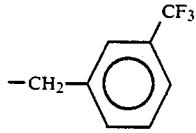 —CH₂-(3-CF₃-C₆H₄) | 1.500 |
| 168 | 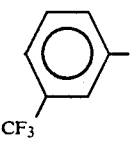 3-CF₃-C₆H₄ | H | —CH₂CH₃ | H | 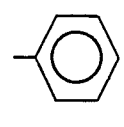 C₆H₅ | oily solid |
| 169 | 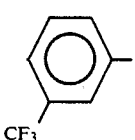 3-CF₃-C₆H₄ | H | —CH₂CH₃ | H | 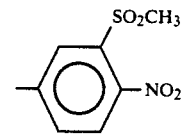 2-NO₂-5-SO₂CH₃-C₆H₃ | oily solid |
| 170 | 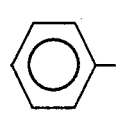 C₆H₅ | H | —CH₂CH₃ | H | 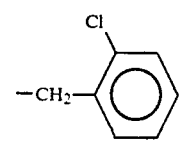 —CH₂-(2-Cl-C₆H₄) | 1.5599 |

TABLE I-continued $$\underset{R}{\overset{R_1}{C}}=N-O-\underset{\underset{O}{\|}}{\overset{R_2}{C}H-C}-N\underset{R_4}{\overset{R_3}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 171 | 3-chloro-4-fluorophenyl | H | —CH₂CH₃ | H | 2-chlorobenzyl (—CH₂-C₆H₄-Cl) | 45-50 |
| 172 | 5-bromo-2-thienyl | H | —CH₂CH₃ | H | 2-(trifluoromethyl)benzyl | 80-83 |
| 173 | 4-fluoro-3-phenoxyphenyl | H | —CH₂CH₃ | H | 2-(trifluoromethyl)benzyl | 1.5375 |
| 174 | 3-chlorophenyl | H | —CH₂CH₃ | H | 2-pyridylmethyl | 50-60 |
| 175 | 3-(trifluoromethyl)phenyl | H | —CH₂CH₃ | H | 2-pyridylmethyl·HCl | oily solid |
| 176 | 4-bromo-5-thienyl | H | —CH₂CH₃ | H | 2-(trifluoromethyl)benzyl | 95-100 |
| 177 | 3-(trifluoromethyl)phenyl | H | —CH₂CH₃ | H | 2-furylmethyl | 1.5080 |
| 178 | 3-(trifluoromethyl)phenyl | H | —CH₂CH₃ | H | —CH₂CHOCH₃ | 1.4858 |
| 179 | 3-(trifluoromethyl)phenyl | H | H | H | —CH₂-C₆H₅ | 92-93 |

TABLE I-continued $$\underset{R}{\overset{R_1}{C}}=N-O-\underset{\underset{O}{\|}}{\overset{R_2}{C}}H-C-N\underset{R_4}{\overset{R_3}{}}$$

| Cmpd. No. | R | $R_1$ | $R_2$ | $R_3$ | $R_4$ | Physical Constant $n_D^{30}$ or m.p. °C. |
|---|---|---|---|---|---|---|
| 180 | 3-CF₃-phenyl | CH₃ | —CH₃ | H | —CH₂-phenyl | 55–60 |
| 181 | 3-CF₃-phenyl | H | —CH₂CH₃ | H | —CH₂-phenyl | 1.5638 |
| 182 | 3-CF₃-phenyl | H | —CH₂CH₃ | H | 2-F-4-CH₃-phenyl | 1.5225 |
| 183 | 3-CF₃-phenyl | H | —CH₂CH₃ | H | 2-CH₃-phenyl | 1.5520 |
| 184 | 3-CF₃-phenyl | H | —CH₂CH₃ | H | 2-CH₃-4-Br-phenyl | 86–89 |
| 185 | 3-CF₃-phenyl | H | —CH₂CH₃ | H | 2-F-4-I-phenyl | dark oil |
| 186 | 3-CF₃-phenyl | H | —CH₂CH₃ | H | 2-Cl-4-I-phenyl | 1.5820 |
| 187 | 3-CF₃-phenyl | H | —CH₂CH₃ | H | 2-Br-4-CH₃-phenyl | 1.5451 |
| 188 | 5-Br-2-thienyl | H | H | H | —CH₂-phenyl | 82–84 |
| 189 | 5-CH₃-2-thienyl | H | H | H | —CH₂-phenyl | 77–78 |

TABLE I-continued $$\underset{R}{\overset{R_1}{\diagdown}}C=N-O-\underset{H}{\overset{R_2}{\underset{|}{C}}}-\underset{\underset{O}{\|}}{C}-N\underset{R_4}{\overset{R_3}{\diagup}}$$

| Cmpd. No. | R | R₁ | R₂ | R₃ | R₄ | Physical Constant n_D^30 or m.p. °C. |
|---|---|---|---|---|---|---|
| 190 | 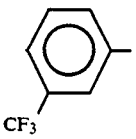 | H | —CH₂CH₃ | H | 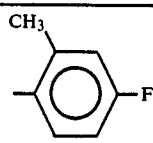 | 68–70 |
| 191 | 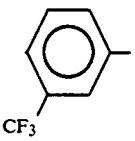 | H | —CH₂CH₃ | H | 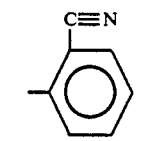 | 45–49 |
| 192 | 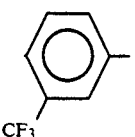 | H | —CH₂CH₃ | H | 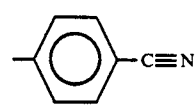 | 1.5536 |
| 193 | 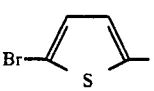 | H | —CH₂CH₃ | H | 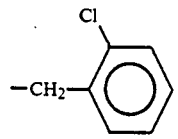 | 82.85 |
| 194 | 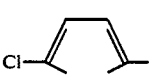 | H | —CH₂CH₃ | H | 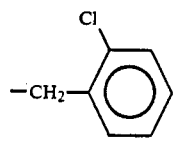 | oily solid |
| 195 | 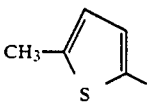 | H | —CH₂CH₃ | H | 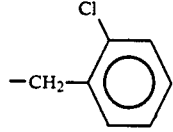 | 88–90 |
| 196 | 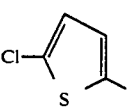 | H | —CH₂CH₃ | H | 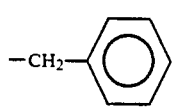 | 45–50 |

The compounds listed in the foregoing Table I were tested for herbicidal activity by various methods and at various rates of application. Some were tested by more than one method or at more than one rate, but at least one method is shown for each compound to exhibit utility. The following examples are for illustrative purposes only and are not intended as necessarily representative of the overall testing performed. As one skilled in the art is aware, in herbicidal testing a significant number of factors that are not readily controllable can affect the results of individual tests. For example, the results may vary depending on environmental factors, such as amount of sunlight and water, soil type, pH of the soil, temperature, and humidity, among other factors. Also, the depth of planting and the application rate of the herbicide, as well as the nature of crops being tested, can affect the results of the test. Results may vary from crop to crop and within the crop varieties. The method and activity are as follows:

Pre-Emergence Herbicidal Evaluation

Flats were filled with sandy loam soil containing a fungicide and fertilizer. The soil was leveled and rows of grassy weeds, broadleaf weeds and yellow nutsedge (Cyperus esculentus), were planted thickly enough so that several seedlings emerged per inch of row. The grassy weeds were: foxtail (Setaria viridis), watergrass (Echinochola crus-galli) and wild oat (Avena fatua). Broadleaf weeds utilized were annual morningglory (Ipomoea spp.) velvetleaf (Abutilon theophrasti) and mustard (Brassica kaber).

One day after planting, the flats were sprayed with a solution of a test compound at a rate of 80 gallons of solution per acre with the compound being applied at a rate of 2 lb/A (1.96 kg/ha), 4 lg/A (4.48 kg/ha), 8 lb/A (8.96 kg/ha) and/or 20 lb/A (22.4 kg/ha).

Solutions of the compounds tested at 2 and 4 lb/A were made by weighing out 333 mg of the test compound into a 60 mL wide-mouth bottle and dissolving it in 25 mL of acetone containing 1% Tween ® 20 (polyoxyethylene sorbitan monolaurate emulsifier). Compounds tested at 8 lb/A were made of solutions consisting of 480 mg of the sample tested, 20 ml of acetone containing 1% Tween ® 20, and 20 mL of water. Compounds tested at 20 lb/A were made of 1200 mg of test compound in 20 mL of acetone containing 1% Tween ® 20 plus 20 mL of water. Additional solvents, not exceeding 5 mL, were used if needed to dissolve the compound. A 20.5 ml aliquot was taken from the stock solution and diluted with 25 mL of an acetone:water mixture (19:1) containing 1% Tween ® 20. This was used as the spray solution.

The flats were returned to the greenhouse after spraying and watered daily by sprinkling. The degree of wee control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; (−) indicates the compound was not tested.

Post-Emergence Herbicidal Evaluation

The soil was prepared and seeded with the same varieties as described for the pre-emergence test. The flats were placed in the green-house at 70°-85° F. and watered by sprinkling. Twelve to fourteen days after planting, the flats were sprayed at a rate of 80 gallons of solution per acre. The compound was applied at the rate of 4 lb/A (4.48 kg/ha). The spray solution wad made up similarly to that described for the pre-emergence evaluation.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE II

| Cmpd. No. | Rate (in lbs) | Pre-Emergent | | | Post-Emergent | | |
|---|---|---|---|---|---|---|---|
| | | CYPES | AVG | AVB | CYPES | AVG | AVB |
| 1 | 4 | 0 | 65 | 97 | 70 | 23 | 67 |
| 2 | 4 | 0 | 33 | 0 | 0 | 0 | 0 |
| 3 | 4 | 0 | 63 | 33 | 0 | 3 | 87 |
| 4 | 4 | 0 | 88 | 100 | 0 | 20 | 67 |
| 5 | 4 | 0 | 33 | 0 | 0 | 0 | 37 |
| 6 | 4 | 70 | 100 | 100 | 80 | 98 | 93 |
| 7 | 4 | 0 | 100 | 100 | 60 | 83 | 87 |
| 8 | 4 | 0 | 37 | 43 | 0 | 37 | 37 |
| 9 | 4 | 0 | 57 | 80 | 0 | 13 | 43 |
| 10 | 4 | 0 | 47 | 83 | 0 | 0 | 60 |

TABLE II-continued

| Cmpd. No. | Rate (in lbs) | Pre-Emergent | | | Post-Emergent | | |
|---|---|---|---|---|---|---|---|
| | | CYPES | AVG | AVB | CYPES | AVG | AVB |
| 11 | 4 | 0 | 50 | 33 | 0 | 0 | 53 |
| 12 | 4 | 0 | 0 | 0 | 0 | 0 | 0 |
| | 8 | 0 | 37 | 30 | 0 | 25 | 3 |
| | 20 | 0 | 37 | 30 | 0 | 27 | 3 |
| 13 | 4 | 0 | 0 | 0 | 0 | 0 | 0 |
| | 8 | 0 | 0 | 5 | 0 | 0 | 3 |
| | 20 | 0 | 0 | 5 | 0 | 0 | 7 |
| 14 | 4 | 75 | 83 | 100 | 0 | 83 | 67 |
| 15 | 4 | 0 | 70 | 93 | 0 | 50 | 43 |
| 16 | 4 | 0 | 0 | 0 | 0 | 0 | 7 |
| | 8 | 0 | 0 | 7 | 0 | 0 | 20 |
| | 20 | 0 | 7 | 27 | 0 | 0 | 25 |
| 17 | 4 | 0 | 33 | 0 | 0 | 0 | 53 |
| 18 | 4 | 0 | 0 | 0 | 0 | 0 | 33 |
| 19 | 4 | 0 | 40 | 33 | 0 | 0 | 57 |
| 20 | 4 | 0 | 0 | 0 | 0 | 0 | 0 |
| | 8 | 0 | 3 | 10 | 0 | 0 | 32 |
| | 20 | 0 | 3 | 33 | 0 | 0 | 45 |
| 21 | 4 | 0 | 0 | 0 | 0 | 0 | 0 |
| | 8 | 0 | 0 | 0 | 0 | 0 | 0 |
| | 20 | 0 | 0 | 0 | 0 | 0 | 0 |
| 22 | 4 | 0 | 33 | 47 | 0 | 0 | 70 |
| 23 | 4 | 0 | 93 | 87 | 50 | 50 | 80 |
| 24 | 4 | 0 | 0 | 0 | 0 | 0 | 40 |
| 25 | 4 | 0 | 40 | 73 | 0 | 0 | 53 |
| 26 | 4 | 0 | 97 | 100 | 80 | 87 | 93 |
| 27 | 4 | 0 | 65 | 93 | 0 | 53 | 67 |
| 28 | 4 | 10 | 83 | 80 | 20 | 67 | 73 |
| 29 | 4 | 0 | 40 | 87 | 30 | 37 | 50 |
| 30 | 4 | 0 | 60 | 68 | 0 | 20 | 57 |
| 31 | 4 | 0 | 37 | 73 | 0 | 0 | 20 |
| 32 | 4 | 0 | 68 | 70 | 0 | 50 | 57 |
| 33 | 4 | 0 | 43 | 40 | 0 | 20 | 50 |
| 34 | 4 | 0 | 77 | 60 | 20 | 27 | 63 |
| 35 | 4 | 0 | 83 | 73 | 0 | 87 | 90 |
| 36 | 4 | 0 | 100 | 100 | 30 | 100 | 100 |
| 37 | 4 | 0 | 83 | 93 | 10 | 73 | 100 |
| 38 | 4 | 0 | 77 | 83 | 0 | 50 | 92 |
| 39 | 4 | 0 | 93 | 100 | 30 | 93 | 100 |
| 40 | 4 | 0 | 73 | 100 | 0 | 57 | 100 |
| 41 | 4 | 0 | 65 | 43 | 0 | 33 | 90 |
| 42 | 4 | 0 | 67 | 57 | 0 | 53 | 75 |
| 43 | 4 | 0 | 67 | 67 | 0 | 20 | 70 |
| 44 | 4 | 0 | 70 | 73 | 0 | 40 | 93 |
| 45 | 4 | 0 | 47 | 47 | 0 | 17 | 67 |
| 46 | 4 | 0 | 95 | 100 | 30 | 90 | 100 |
| 47 | 4 | 0 | 23 | 27 | 0 | 7 | 87 |
| 48 | 4 | 0 | 23 | 27 | 0 | 0 | 63 |
| 49 | 4 | 0 | 80 | 95 | 0 | 68 | 98 |
| 50 | 4 | 0 | 0 | 0 | 0 | 0 | 23 |
| 51 | 4 | 0 | 72 | 77 | 0 | 77 | 98 |
| 52 | 4 | 0 | 57 | 0 | 0 | 27 | 0 |
| 53 | 4 | 0 | 68 | 80 | 0 | 40 | 73 |
| 54 | 4 | 0 | 80 | 82 | 0 | 57 | 80 |
| 55 | 4 | 0 | 98 | 98 | 40 | 100 | 87 |
| 56 | 4 | 0 | 78 | 83 | 0 | 57 | 90 |
| 57 | 4 | 0 | 30 | 10 | 0 | 27 | 53 |
| 58 | 4 | 20 | 77 | 100 | 20 | 60 | 70 |
| 59 | 4 | 0 | 97 | 100 | 30 | 83 | 93 |
| 60 | 4 | 0 | 87 | 65 | 0 | 17 | 82 |
| 61 | 4 | 0 | 95 | 90 | 0 | 60 | 97 |
| 62 | 4 | 0 | 33 | 40 | 0 | 17 | 60 |
| 63 | 4 | 0 | 98 | 87 | 10 | 98 | 100 |
| 64 | 4 | 0 | 68 | 63 | 0 | 0 | 75 |
| 65 | 4 | 0 | 97 | 97 | 30 | 95 | 100 |
| 66 | 4 | 0 | 67 | 50 | 0 | 40 | 77 |
| 67 | 4 | 40 | 83 | 87 | 65 | 73 | 100 |
| 68 | 4 | 0 | 98 | 87 | 0 | 95 | 100 |
| 69 | 4 | 10 | 97 | 98 | 0 | 95 | 100 |
| 70 | 4 | 0 | 70 | 62 | 0 | 33 | 67 |
| 71 | 4 | 0 | 77 | 70 | 0 | 60 | 88 |
| 72 | 4 | 0 | 53 | 68 | 0 | 27 | 40 |
| 73 | 4 | 0 | 37 | 57 | 0 | 0 | 0 |
| 74 | 4 | 0 | 28 | 33 | 0 | 40 | 0 |
| 75 | 4 | 0 | 43 | 58 | 0 | 0 | 0 |
| 76 | 4 | 0 | 78 | 43 | 0 | 53 | 47 |
| 77 | 4 | 0 | 93 | 100 | 0 | 98 | 88 |
| 78 | 4 | 0 | 73 | 67 | 0 | 43 | 63 |

TABLE II-continued

| Cmpd. No. | Rate (in lbs) | Pre-Emergent CYPES | AVG | AVB | Post-Emergent CYPES | AVG | AVB |
|---|---|---|---|---|---|---|---|
| 79 | 4 | 0 | 70 | 40 | 0 | 47 | 68 |
| 80 | 4 | 0 | 100 | 95 | 0 | 100 | 100 |
| 81 | 4 | 0 | 47 | 53 | 0 | 0 | 0 |
| 82 | 4 | 0 | 77 | 82 | 20 | 70 | 93 |
| 83 | 4 | 0 | 73 | 80 | 0 | 57 | 87 |
| 84 | 4 | 0 | 23 | 43 | 0 | 0 | 0 |
| 85 | 4 | 0 | 67 | 67 | 0 | 17 | 73 |
| 86 | 4 | 0 | 27 | 7 | 0 | 0 | 0 |
| 87 | 4 | 0 | 60 | 67 | 0 | 0 | 0 |
| 88 | 4 | 0 | 100 | 98 | 0 | 100 | 100 |
| 89 | 4 | 0 | 99 | 88 | 0 | 95 | 87 |
| 90 | 4 | 0 | 67 | 67 | 0 | 17 | 73 |
| 91 | 4 | 0 | 37 | 0 | 0 | 0 | 0 |
| 92 | 4 | 0 | 80 | 73 | 0 | 7 | 90 |
| 93 | 4 | 0 | 78 | 87 | 0 | 50 | 60 |
| 94 | 4 | 30 | 67 | 90 | 0 | 20 | 37 |
| 95 | 4 | 20 | 81 | 87 | 0 | 33 | 73 |
| 96 | 4 | 20 | 83 | 86 | 30 | 85 | 57 |
| 97 | 4 | 20 | 76 | 86 | 0 | 27 | 72 |
| 98 | 4 | 0 | 36 | 7 | 0 | 0 | 0 |
| 99 | 4 | 0 | 40 | 2 | 0 | 0 | 0 |
| 100 | 4 | 30 | 87 | 98 | 10 | 73 | 88 |
| 101 | 4 | 80 | 98 | 100 | 50 | 73 | 77 |
| 102 | 4 | 0 | 40 | 28 | 0 | 0 | 0 |
| 103 | 4 | 0 | 10 | 27 | 0 | 0 | 7 |
| 104 | 4 | 0 | 0 | 0 | 0 | 0 | 0 |
|  | 8 | 0 | 0 | 0 | 0 | 0 | 0 |
|  | 20 | 0 | 0 | 0 | 0 | 0 | 0 |
| 105 | 4 | 0 | 96 | 57 | 0 | 67 | 95 |
| 106 | 4 | 0 | 47 | 57 | 0 | 63 | 93 |
| 107 | 4 | 0 | 90 | 97 | 30 | 92 | 85 |
| 108 | 4 | 0 | 93 | 97 | 30 | 93 | 83 |
| 109 | 4 | 0 | 93 | 98 | 40 | 78 | 88 |
| 110 | 4 | 0 | 98 | 98 | 10 | 95 | 88 |
| 111 | 4 | 0 | 80 | 95 | 0 | 77 | 82 |
| 112 | 4 | 0 | 97 | 97 | 0 | 95 | 75 |
| 113 | 4 | 0 | 83 | 53 | 0 | 63 | 53 |
| 114 | 4 | 10 | 97 | 98 | 10 | 100 | 100 |
| 115 | 4 | 10 | 98 | 93 | 20 | 100 | 100 |
| 116 | 4 | 0 | 73 | 40 | 0 | 20 | 40 |
| 117 | 4 | 0 | 0 | 0 | 0 | 0 | 0 |
|  | 8 | 0 | 0 | 0 | 0 | 0 | 0 |
| 118 | 4 | 0 | 37 | 33 | 0 | 0 | 0 |
| 119 | 4 | 0 | 0 | 0 | 0 | 0 | 0 |
|  | 8 | 0 | 37 | 48 | 0 | 12 | 37 |
| 120 | 4 | 0 | 0 | 0 | 0 | 0 | 0 |
|  | 8 | 0 | 0 | 0 | 0 | 10 | 30 |
| 121 | 4 | 0 | 100 | 93 | 0 | 87 | 100 |
| 122 | 4 | 0 | 100 | 97 | 0 | 80 | 100 |
| 123 | 4 | 0 | 47 | 73 | 0 | 17 | 53 |
| 124 | 4 | 0 | 80 | 100 | 0 | 78 | 93 |
| 125 | 4 | 0 | 73 | 47 | 0 | 0 | 0 |
| 126 | 4 | 0 | 73 | 47 | 30 | 10 | 43 |
| 127 | 4 | 0 | 77 | 93 | 20 | 68 | 87 |
| 128 | 4 | 20 | 70 | 77 | 60 | 40 | 60 |
| 129 | 4 | 0 | 100 | 95 | 60 | 43 | 50 |
| 130 | 4 | 30 | 93 | 100 | 70 | 63 | 97 |
| 131 | 4 | 0 | 33 | 0 | 0 | 0 | 0 |
| 132 | 4 | 0 | 100 | 100 | 10 | 83 | 80 |
| 133 | 4 | 0 | 93 | 43 | 0 | 7 | 40 |
| 134 | 4 | 0 | 67 | 40 | 0 | 0 | 0 |
| 135 | 4 | 0 | 67 | 43 | 0 | 0 | 37 |
| 136 | 4 | 0 | 77 | 95 | 0 | 60 | 67 |
| 137 | 4 | 70 | 95 | 100 | 80 | 87 | 87 |
| 138 | 4 | 0 | 80 | 100 | 20 | 70 | 77 |
| 139 | 4 | 0 | 67 | 47 | 20 | 43 | 57 |
| 140 | 4 | 20 | 73 | 80 | 30 | 50 | 77 |
| 141 | 4 | 0 | 73 | 40 | 0 | 7 | 40 |
| 142 | 4 | 0 | 100 | 93 | 30 | 73 | 67 |
| 143 | 4 | 30 | 70 | 82 | 80 | 53 | 63 |
| 144 | 4 | 50 | 97 | 93 | 30 | 67 | 83 |
| 145 | 4 | 60 | 73 | 67 | 70 | 67 | 60 |
| 146 | 4 | 0 | 97 | 73 | 0 | 63 | 97 |
| 147 | 4 | 0 | 100 | 93 | 0 | 83 | 87 |
| 148 | 4 | 0 | 98 | 77 | 0 | 53 | 100 |
| 149 | 4 | 0 | 65 | 80 | 0 | 67 | 60 |
| 150 | 4 | 0 | 33 | 33 | 0 | 7 | 57 |
| 151 | 4 | 30 | 100 | 100 | 30 | 90 | 87 |
| 152 | 4 | 0 | 93 | 73 | 0 | 40 | 93 |
| 153 | 4 | 0 | 70 | 67 | 0 | 43 | 97 |
| 154 | 4 | 30 | 80 | 87 | 30 | 80 | 92 |
| 155 | 4 | 0 | 93 | 57 | 0 | 13 | 70 |
| 156 | 4 | 30 | 100 | 37 | 0 | 30 | 67 |
| 157 | 4 | 0 | 43 | 33 | 0 | 10 | 67 |
| 158 | 4 | 0 | 50 | 40 | 0 | 20 | 47 |
| 159 | 4 | 0 | 97 | 93 | 0 | 70 | 73 |
| 160 | 4 | 30 | 73 | 93 | 30 | 40 | 53 |
| 161 | 4 | 0 | 67 | 87 | 0 | 62 | 60 |
| 162 | 4 | 0 | 60 | 50 | 0 | 30 | 60 |
| 163 | 4 | 30 | 70 | 80 | 30 | 67 | 87 |
| 164 | 4 | 0 | 47 | 37 | 0 | 23 | 60 |
| 165 | 4 | 0 | 77 | 93 | 0 | 77 | 85 |
| 166 | 2 | 0 | 40 | 40 | 0 | 3 | 7 |
| 167 | 2 | 0 | 87 | 100 | 0 | 53 | 80 |
| 168 | 2 | 10 | 67 | 67 | 20 | 50 | 73 |
| 169 | 2 | 0 | 70 | 53 | 0 | 23 | 53 |
| 170 | 2 | 0 | 33 | 27 | 0 | 3 | 17 |
| 171 | 2 | 0 | 67 | 47 | 0 | 17 | 70 |
| 172 | 2 | 0 | 93 | 100 | 0 | 67 | 93 |
| 173 | 2 | 0 | 0 | 0 | 0 | 0 | 0 |
| 174 | 2 | 0 | 90 | 97 | 30 | 93 | 87 |
| 175 | 2 | 30 | 100 | 100 | 50 | 97 | 90 |
| 176 | 2 | 0 | 43 | 53 | 0 | 0 | 0 |
| 177 | 2 | 0 | 13 | 20 | 0 | 0 | 33 |
| 178 | 2 | 70 | 87 | 87 | 20 | 47 | 77 |
| 179 | 2 | 20 | 88 | 80 | 40 | 43 | 67 |
| 180 | 2 | 0 | 0 | 0 | 0 | 0 | 0 |
| 181 | 2 | 80 | 98 | 73 | 0 | 47 | 47 |
| 182 | 2 | 0 | 97 | 92 | 0 | 82 | 53 |
| 183 | 2 | 0 | 100 | 100 | 0 | 27 | 30 |
| 184 | 2 | 0 | 98 | 93 | 0 | 60 | 43 |
| 185 | 2 | 0 | 98 | 75 | 0 | 0 | 37 |
| 186 | 2 | 0 | 23 | 10 | 0 | 0 | 47 |
| 187 | 2 | 0 | 93 | 50 | 0 | 30 | 53 |
| 188 | 2 | 0 | 0 | 0 | 0 | 0 | 0 |
| 189 | 2 | 0 | 0 | 0 | 0 | 0 | 0 |
| 190 | 2 | 40 | 98 | 100 | 60 | 85 | 88 |
| 191 | 2 | 0 | 40 | 23 | 0 | 0 | 0 |
| 192 | 2 | 0 | 70 | 57 | 0 | 47 | 73 |
| 193 | 2 | 0 | 68 | 40 | 0 | 30 | 53 |
| 194 | 2 | 0 | 73 | 53 | 0 | 57 | 60 |
| 195 | 2 | 0 | 40 | 28 | 0 | 0 | 37 |
| 196 | 2 | 40 | 73 | 70 | 60 | 77 | 57 |

Although Compound No. 104 showed no apparent activity in our 2 lb and 4 lb screens above, it did exhibit some activity in our controlled light post-emergence screen described below. Following is a table of its activity.

Controlled Light Post-emergence Multi-Weed/Multi-Crop Evaluation

The soil was prepared and seeded as described for the pre-emergence test. Flats containing seeds of broadleaf species were placed in the greenhouse 21 days, and flats containing seeds of grass species were placed in the greenhouse 14 days before spraying at the same rates as in the pre-emergence evaluation.

After spraying, the flats were returned to the greenhouse and watered daily. Three to four weeks after treatment, the degree of control was estimated and the percent control ratings were assigned on the same basis as for the pre-emergence evaluation.

The following Table III contains the results of these tests in terms of average control of the four grasses, five broadleaf weeds and three crops in these evaluations.

TABLE III

| Cmpd. No. | Rate lb/A | Average Grasses | Post-Emergence Average Broadleaf | Sugar-beet | Barley | Wheat |
|---|---|---|---|---|---|---|
| 104 | 4 | 0 | 24 | 30 | 0 | 0 |

The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agents.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic napthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulations.

The compounds of the present invention are also useful when combined with other herbicides and/or defoliants, dessicants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB and silvex;

carbamate herbicides such as propham, chlorpropham, swep and barban;

thiocarbamate and dithiocarbamate herbicides such as CDEC, metham-sodium, EPTC, diallate, PEBC and vernolate;

substituted urea herbicides such as norea, dichloral urea, chloroxuron, cyclouron, frnuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6-trichlorophenylacetic acid and 2,4-dichloro-3-nitrobenzoic acid;

and such compounds as aminotriazole, maleic hydrazide, phenylmercury acetate, endothal, tehcnical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMIT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sensone, terbacil, terbutol, TCBA, alachlor, nitralin, sodium tetraborate, calcium cyanamide, S,S,S-tributylphosphorotrithiolate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: | 5 parts active compound |
| | 0.25 part epichlorohydrin |
| | 0.25 part cetyl polyglycol ether |
| | 3.5 parts polyethylene glycol |
| | 91 parts kaolin (particle size 0.3-0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

wettable powders:

| 70% | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40% | 40 parts active compound |
| | 5 parts sodium lignin sulfonate |

| | -continued |
|---|---|
| | 1 part sodium dibutylnaphthalenesulfonic acid |
| | 54 parts silicic acid |
| 25% | 25 parts active compound |
| | 4.5 parts calcium lignin sulfate |
| | 1.9 parts Champagne chalk/hydroxyethyl cellulose (1:1) |
| | 1.5 parts sodium dibutylnaphthalenesulfonate |
| | 19.5 parts silicic acid |
| | 19.5 parts Champagne chalk |
| | 28.1 parts kaolin |
| 25% | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10% | 10 parts active compound |
| | 3 parts of a mixture of sodium salts of saturated fatty alcohol sulfates |
| | 5 parts of naphthalenesulfonic acid/formaldehyde condensate |
| | 82 parts kaolin |

These wettable powders are prepared by intimately mixing the active compounds with the additives in suitable mixers, and grinding the resulting mixtures in mills or rollers.

25% emulsifiable concentrate:
25 parts active substance
2.5 parts epoxidized vegetable oil
10 parts of an alkylarylsulfonate/fatty alcohol polyglycol ether mixture
5 parts dimethylformamide
57.5 parts xyxlene

What is claimed is:

1. A compound having the formula

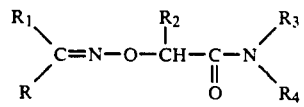

wherein:
R is phenyl or phenyl substituted with one or more $C_1-C_6$ alkyl, $C_1-C_4$ alkoxy, halo, $C_1-C_6$ haloalkyl, cyano, nitro or $C_1-C_6$ alkylsulfonyl;
$R_1$ is hydrogen or $C_1-C_6$ alkyl;
$R_2$ is hydrogen, $C_1-C_6$ alkyl, $C_3-C_6$ cycloalkyl or lower alkylalkoxy; and
one of $R_3$ and $R_4$ is pyridyl or pyridyl substituted with one or more halogen or $C_1-C_6$ alkyl; and the other is hydrogen, $C_1-C_6$ alkyl, $C_2-C_6$ alkenyl or $C_2-C_6$ alkynyl.

2. A compound according to claim 1 wherein R is phenyl or phenyl substituted with one or more fluorine, chlorine, bromine, iodine or trifluoromethyl; $R_1$ is hydrogen or methyl; $R_2$ is methoxymethyl or ethyl; $R_3$ is hydrogen or ethyl; and $R_4$ is methyl-2-pyridyl.

3. A compound according to claim 2 wherein $R_1$ is hydrogen, $R_2$ is ethyl, and $R_3$ is hydrogen.

4. A compound according to claim 3 wherein R is trifluoromethylphenyl or chlorophenyl and $R_4$ is pyridyl.

5. A compound according to claim 1 wherein $R_4$ is 2-methylpyridyl.

6. An herbicidal composition comprising:
(a) an herbicidally effective amount of a compound having the formula $$\begin{array}{c} R_1 \\ \diagdown \\ R \diagup \end{array} C=N-O-CH-C-N \begin{array}{c} R_3 \\ \diagup \\ \diagdown R_4 \end{array}$$
$$\phantom{xxxxxxxxxxxxxxxx} | \phantom{xxxx} \| $$
$$\phantom{xxxxxxxxxxxxxxxxx} R_2 \phantom{xx} O $$

wherein:
R is phenyl or phenyl substituted with one or more $C_1$-$C_6$ alkyl, $C_1$-$C_4$ alkoxy, halo, $C_1$-$C_6$ haloalkyl, cyano, nitro or $C_1$-$C_6$ alkylsulfonyl;

$R_1$ is hydrogen or $C_1$-$C_6$ alkyl;

$R_2$ is hydrogen, $C_1$-$C_6$ alkyl, $C_3$-$C_6$ cycloalkyl or lower alkylalkoxy; and one of $R_3$ and $R_4$ is pyridyl or pyridyl substituted with one or more halogen or $C_1$-$C_6$ alkyl; and the other is hydrogen, $C_1$-$C_6$ alkyl, $C_2$-$C_6$ alkenyl or $C_2$-$C_6$ alkynyl; and (b) an inert diluent carrier therefor.

7. A composition according to claim 6 wherein R is phenyl or phenyl substituted with one or more fluorine, chlorine, bromine, iodine or trifluoromethyl; $R_1$ is hydrogen or methyl; $R_2$ is methoxymethyl or ethyl; $R_3$ is hydrogen or ethyl; and $R_4$ is methyl-2-pyridyl.

8. An herbicidal composition according to claim 7 wherein $R_1$ is hydrogen, $R_2$ is ethyl, and $R_3$ is hydrogen.

9. An herbicidal composition according to claim 8 wherein R is trifluoromethylphenyl or chlorophenyl and $R_4$ is pyridyl.

10. An herbicidal composition according to claim 6 wherein $R_4$ is 2-methylpyridyl.

11. A method of controlling undesirable vegetation comprising applying to said vegetation or to the locus thereof an herbicidally effective amount of a compound having the formula $$\begin{array}{c} R_1 \\ \diagdown \\ R \diagup \end{array} C=N-O-CH-C-N \begin{array}{c} R_3 \\ \diagup \\ \diagdown R_4 \end{array}$$
$$\phantom{xxxxxxxxxxxxxxxx} | \phantom{xxxx} \| $$
$$\phantom{xxxxxxxxxxxxxxxxx} R_2 \phantom{xx} O $$

wherein:
R is phenyl or phenyl substituted with one or more $C_1$-$C_6$ alkyl, $C_1$-$C_4$ alkoxy, halo, $C_1$-$C_6$ haloalkyl, cyano, nitro or $C_1$-$C_6$ alkylsulfonyl;

$R_1$ is hydrogen or $C_1$-$C_6$ alkyl;

$R_2$ is hydrogen, $C_1$-$C_6$ alkyl, $C_3$-$C_6$ cycloalkyl or lower alkylalkoxy; and one of $R_3$ and $R_4$ is pyridyl or pyridyl substituted with one or more halogen or $C_1$-$C_6$ alkyl; and the other is hydrogen, $C_1$-$C_6$ alkyl, $C_2$-$C_6$ alkenyl or $C_2$-$C_6$ alkynyl.

12. The method according to claim 11 wherein R is phenyl or phenyl substituted with one or more fluorine, chlorine, bromine, iodine or trifluoromethyl; $R_1$ is hydrogen or methyl; $R_2$ is methoxymethyl or ethyl; $R_3$ is hydrogen or ethyl; and $R_4$ is methyl-2-pyridyl.

13. The method according to claim 12 wherein $R_1$ is hydrogen, $R_2$ is ethyl, and $R_3$ is hydrogen.

14. The method according to claim 13 wherein R is trifluoromethylphenyl or chlorophenyl and $R_4$ is pyridyl.

15. The method according to claim 11 wherein $R_4$ is 2-methylpyridyl.

* * * * *